(12) United States Patent
Knappe et al.

(10) Patent No.: US 8,802,068 B2
(45) Date of Patent: Aug. 12, 2014

(54) NON-WEIGHING HAIR PREPARATIONS

(75) Inventors: Thorsten Knappe, Schenefeld (DE);
Bernd Richters, Hamburg (DE); Helga van Flodrop, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/517,707

(22) Filed: Jun. 14, 2012

(65) Prior Publication Data

US 2012/0251473 A1 Oct. 4, 2012

Related U.S. Application Data

(63) Continuation of application No. PCT/EP2010/067459, filed on Nov. 15, 2010.

(30) Foreign Application Priority Data

Dec. 15, 2009 (DE) .......................... 10 2009 054 665

(51) Int. Cl.
*A61Q 5/12* (2006.01)

(52) U.S. Cl.
USPC ..................................... 424/70.12; 424/70.27

(58) Field of Classification Search
None
See application file for complete search history.

(56) References Cited

U.S. PATENT DOCUMENTS

| 5,490,890 A | * | 2/1996 | Morrison ........................ 156/66 |
| 5,490,980 A | * | 2/1996 | Richardson et al. ......... 424/94.6 |
| 2006/0216258 A1 | * | 9/2006 | Singleton et al. .......... 424/70.12 |
| 2011/0110992 A1 | * | 5/2011 | Garrison et al. .............. 424/401 |

* cited by examiner

*Primary Examiner* — Carlos Azpuru
*Assistant Examiner* — Casey Hagopian
(74) *Attorney, Agent, or Firm* — David K. Benson

(57) ABSTRACT

An agent for treating keratin-comprising fibers, in particular human hair, which includes in a cosmetic carrier at least one cyclic siloxane, at least one C8 to C30 alkyl PEG/PPG dimethicone, and at least one cationic protein hydrolysate.

8 Claims, No Drawings

NON-WEIGHING HAIR PREPARATIONS

CROSS-REFERENCES TO RELATED APPLICATIONS

This application is a continuation of PCT/EP2010/067459, filed on Nov. 15, 2010, which claims priority under 35 U.S.C. §119 to DE 10 2009 054 665.0 filed on Dec. 15, 2009, both of which are hereby incorporated by reference.

FIELD OF THE INVENTION

The present invention generally relates to an agent for treating keratin-containing fibers, in particular human hair, and more particularly relates to two-phase hair treatment agents.

BACKGROUND OF THE INVENTION

Care-providing products for keratinic fibers often exhibit the disadvantage that they weigh the hair down and thereby reduce its fullness. This problem occurs in particular with products that are left in the hair (called "leave-on" products). In contrast thereto, products that are rinsed out shortly after being applied (called "rinse-off" products) often do not have sufficient care-providing potential. There is a continuing need for hair treatment agents that provide lasting care to the hair and improve shine and softness, without weighing the hairstyle. Ideally this can be achieved with products that both can be rinsed out again from the hair after a relatively short time, and can remain on the hair.

Usual two-phase care-providing products of the existing art exhibit appreciable instabilities in the context of a high mechanical stress. These stresses can be, for example, shaking prior to use, or discharge from the spray head, since large shear forces occur in these contexts. The usual compositions are, however, not sufficiently stable even at low temperatures, in particular if a high mechanical stress additionally occurs at low temperatures. There is therefore a continuing need to improve the stability of such compositions in accordance with the existing art.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has now been found, unforeseeably, that care-providing agents for hair that contain an aqueous carrier can be significantly improved, in terms of their care-providing potential and their effect on fullness and volume and on stability with regard to high mechanical stresses and low temperatures, if they include at least one cyclic silicone and at least one C8 to C30 alkyl PEG/PPG dimethicone. Instabilities may be further avoided particularly effectively if cationic protein hydrolysates are used as care-providing constituents in the formulations.

Accordingly, a hair treatment agent according to the present invention includes, based on its weight, at least 70 wt. % water, 0.1 to 1.5 wt. % of at least one silicone-based water-in-oil emulsifier from the group of C8 to C30 alkyl PEG/PPG dimethicone, 1 to 10 wt. % cyclic siloxane, and at least 0.1 to 5 wt. % of a cationic protein hydrolysate.

Furthermore, a method for providing care to human hair includes applying such a hair treatment agent onto the hair, leaving the agent on the hair for a contact time from 10 to 600 seconds, preferably from 30 to 150 seconds, and then rinsing the hair out.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject matter of the present invention is hair treatment agents including, based on their weight,
a) at least 70 wt. % water,
b) 0.1 to 1.5 wt. % of at least one silicone-based water-in-oil emulsifier from the group of C8 to C30 alkyl PEG/PPG dimethicone,
c) 1 to 10 wt. % cyclic siloxane, and
d) at least 0.1 to 5 wt. % of a cationic protein hydrolysate.

The agents according to the present invention include at least 70 wt. % water. Agents preferred according to the present invention are characterized in that they include, based on their weight, 75 to 97.5 wt. %, by preference 77.5 to 95 wt. %, more preferably 80 to 92.5 wt. %, and in particular 82.5 to 90 wt. % water.

The agents according to the present invention further include at least one silicone-based water-in-oil emulsifier from the group of C8 to C30 alkyl PEG/PPG dimethicones, the previous INCI name of which was Dimethicone Polyols, having the current INCI names C8-C30 PEG-x Dimethicone (where x=2 to 20, preferably 3 to 17, particularly preferably 7 to 12), PEG/PPG a/b Dimethicone (where a and b are mutually independent and a denotes numbers from 2 to 30, preferably 3 to 30, and particularly preferably 5 to 20, in particular 7 to 18, and b denotes numbers from 0 to 30, preferably 0 to 20 and particularly preferably from 0 to 15, and in particular from 0 to 12). Within the group of C8 to C30 alkyl PEG/PPG dimethicones, those that carry an alkyl group from C8 to C22, particularly preferably from C12 to C22, and in particular from C12 to C18, are preferred. The most preferred C8 to C30 alkyl PEG/PPG dimethicones are lauryl, myristyl, cetyl, and stearyl PEG/PPG dimethicones. These most preferred dimethicones include as PEG/PPG a/b dimethicones, for a and b mutually independently in each case, having values for a from 2 to 30, preferably 3 to 30 and particularly preferably 5 to 20, in particular 7 to 18, and b [denotes] values from 0 to 30, preferably 0 to 20 and particularly preferably from 0 to 15, and in particular from 0 to 12. Most highly preferred, for example, are the commercial products Abil® EM-90, Microcare Silicone E 1016 (Thor Co.), Dow Corning® Q2-5200, or mixtures thereof.

Preferred agents according to the present invention include silicone-based water-in-oil emulsifiers from the group of C8 to C30 alkyl PEG/PPG dimethicones preferably within narrow quantity ranges. The agents according to the present invention preferred here are those that include, based on their weight, 0.15 to 1.25 wt. %, by preference 0.2 to 1.0 wt. %, more preferably 0.25 to 0.75 wt. %, and in particular 0.3 to 0.5 wt. % of at least one silicone-based water-in-oil emulsifier from the group of C8 to C30 alkyl PEG/PPG dimethicones.

Cyclic siloxanes, which according to INCI are referred to as Cyclomethicone, are usable with preference according to the present invention. Cosmetic or dermatologic preparations that include at least one silicone of formula (Si-4)

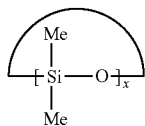

(Si-4)

in which x denotes a number from 3 to 200, by preference from 3 to 10, more preferably from 3 to 7, and in particular 3, 4, 5, or 6, are preferred here. Most preferred is Cyclopentasiloxane (CAS 2,4,6,8,10-pentamethylcyclopentasiloxane), with x=5.

The agents according to the present invention include at least 1 to 10 wt. % of the cyclic siloxanes. Particularly preferred agents according to the present invention are characterized in that they include, based on their weight, 1.5 to 9.5 wt. %, by preference 1.75 to 9 wt. %, more preferably 2.0 to 8.5 wt. %, even more preferably 2.5 to 8.0 wt. %, even more preferably 3.0 to 7.5 wt. %, and in particular 3.5 to 7.5 wt. % cyclic siloxanes.

In addition to the silicone-based water-in-oil emulsifier from the group of C8 to C30 alkyl PEG/PPG dimethicones, the agents according to the present invention include 0.01 to 5 wt. % of at least one silicone-free emulsifier.

Oil-in-water emulsifiers preferred according to the present invention have an HLB value of at least 8, the entire oil-in-water emulsifier system having by preference a weight-average (weight averaged) HLB value in the range from 11 to 17, preferably 13.5 to 15.5. These emulsifiers are ones commonly known to the skilled artisan, such as those listed, for example, in Kirk-Othmer, "Encyclopedia of Chemical Technology," 3rd ed., 1979, Vol. 8, pp. 913-916. For ethoxylated products, the HLB value is calculated according to the formula HLB=(100-L): 5, where L is the weight proportion of the lipophilic groups, i.e. the fatty alkyl or fatty acyl groups, in the ethylene oxide adducts, expressed as a percentage by weight.

When selecting silicone-free oil-in-water emulsifiers suitable according to the present invention, preferably nonionic oil-in-water emulsifiers, it is particularly preferred to use a mixture of oil-in-water emulsifiers, preferably nonionic oil-in-water emulsifiers, in order to allow optimum adjustment of the stability of the compositions according to the present invention. The individual emulsifier components supply a portion of the total HLB value or average HLB value of the oil-in-water emulsifier mixture in accordance with their weight proportion in terms of the total weight of the oil-in-water emulsifiers. In preferred fashion according to the present invention, the weight-average HLB value of the oil-in-water emulsifier system is equal to 11 to 17, preferably 12 to 15, and particularly preferably 13.5 to 15.5. To achieve such HLB values, it is preferred to combine oil-in-water emulsifiers from the HLB value ranges 10 to 14, 14 to 16, and optionally 15 to 17 with one another. The oil-in-water emulsifier mixtures (or oil-in-water emulsifier systems) can of course also include emulsifiers, preferably nonionic emulsifiers, having HLB values in the range from >7 to 10 and 17 to 20; such emulsifier mixtures can likewise be preferred according to the present invention. In another preferred embodiment, however, the compositions according to the present invention can also include only a single oil-in-water emulsifier having an HLB value in the range from 11 to 17, preferably 12 to 15, and particularly preferably 13 to 14.

Preferred agents according to the present invention are characterized in that the silicone-free oil-in-water emulsifiers are selected from ethoxylated $C_8$ to $C_{24}$ alkanols having an average of 8 to 100 mol ethylene oxide per mol, ethoxylated $C_8$ to $C_{24}$ carboxylic acids having an average of 8 to 100 mol ethylene oxide per mole, glycerol mono- and/or diesters, ethoxylated with an average of 20 to 100 mol ethylene oxide per mol, of linear saturated and unsaturated $C_{12}$ to $C_{30}$ carboxylic acids, which can be hydroxylated, in particular those of myristic acid, palmitic acid, stearic acid, 12-hydroxystearic acid, or mixtures of said fatty acids, sorbitan monoesters, ethoxylated with an average of 20 to 100 mol ethylene oxide per mol, of linear saturated and unsaturated $C_{12}$ to $C_{30}$ carboxylic acids, which can be hydroxylated, in particular those of myristic acid, palmitic acid, stearic acid, 12-hydroxystearic acid, or mixtures of said fatty acids, silicone copolyols having ethylene oxide units or having ethylene oxide and propylene oxide units, alkyl mono- and oligoglycosides having 8 to 22 carbon atoms in the alkyl residue and ethoxylated analogs thereof, ethoxylated sterols, partial esters of polyglycerols having n=2 to 10 glycerol units and esterified with 1 to 4 saturated or unsaturated, linear or branched, optionally hydroxylated $C_8$ to $C_{30}$ fatty acid residues, provided they have an HLB value of more than 7, as well as mixtures of the aforesaid substances.

The ethoxylated $C_8$ to $C_{24}$ alkanols have the formula $R^1O(CH_2CH_2O)_nH$, where $R^1$ denotes a linear or branched alkyl and/or alkenyl residue having 8 to 24 carbon atoms, and n (the average number of ethylene oxide units per molecule) denotes numbers from 8 to 100, by preference 8 to 30 mol ethylene oxide per 1 mol capryl alcohol, 2-ethylhexyl alcohol, capric alcohol, lauryl alcohol, isotridecyl alcohol, tridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and brassidyl alcohol, as well as technical mixtures thereof. Adducts of 8 to 100 mol ethylene oxide with technical fatty alcohols having 12 to 18 carbon atoms, for example coconut, palm, palm kernel, or tallow alcohol, are also suitable.

The ethoxylated $C_8$ to $C_{24}$ carboxylic acids have the formula $R^1O(CH_2CH_2O)_nH$, where $R^1O$ denotes a linear or branched acyl residue having 8 to 24 carbon atoms, and n (the average number of ethylene oxide units per molecule) denotes numbers from 8 to 100, by preference 10 to 30 mol ethylene oxide per 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselinic acid, arachidic acid, gadoleic acid, behenic acid, erucic acid, and brassidic acid, as well as technical mixtures thereof. Adducts of 10 to 100 mol ethylene oxide with technical fatty acids having 12 to 18 carbon atoms, for example coconut, palm, palm kernel, or tallow fatty acid, are also suitable. PEG-50 monostearate, PEG-100 monostearate, PEG-50 monooleate, PEG-100 monooleate, PEG-50 monolaurate, and PEG-100 monolaurate are particularly preferred.

It is particularly preferred to use the $C_{12}$ to $C_{18}$ alkanols or the $C_{12}$ to $C_{18}$ carboxylic acids respectively having 8 to 30 units of ethylene oxide per molecule, as well as mixtures of said substances, in particular laureth-8, laureth-10, laureth-12, laureth-20, trideceth-8, trideceth-9, trideceth-10, trideceth-12, trideceth-20, ceteth-10, ceteth-12, ceteth-20, ceteth-30, steareth-10, steareth-12, steareth-20, steareth-30, ceteareth-10, ceteareth-12, ceteareth-20, ceteareth-30, laureth-12, and beheneth-20.

Preferred glycerol mono- and/or diesters, ethoxylated with an average of 20 to 100 mol ethylene oxide per mol, of linear saturated and unsaturated $C_{12}$ to $C_{30}$ carboxylic acids, which can be hydroxylated, are selected from PEG-20 Hydrogenated Castor Oil, PEG-40 Hydrogenated Castor Oil, and PEG-60 Hydrogenated Castor Oil.

Preferred sorbitan monoesters, ethoxylated with an average of 20 to 100 mol ethylene oxide per mol, of linear saturated and unsaturated $C_{12}$ to $C_{30}$ carboxylic acids, which can be hydroxylated, are selected from Polysorbate-20, Polysorbate-40, Polysorbate-60, and Polysorbate-80.

$C_8$ to $C_{22}$ alkyl mono- and oligoglycosides are also used by preference. $C_8$ to $C_{22}$ alkyl mono- and oligoglycosides represent known, commercially usual surfactants and emulsifiers. They are manufactured, in particular, by reacting glucose or oligosaccharides with primary alcohols having 8 to 22 carbon atoms. In terms of the glycoside residue, both monoglycosides, in which a cyclic sugar residue is glycosidically bound to the fatty alcohol, and oligomeric glycosides having a degree of oligomerization of up to approximately 8, by preference 1 to 2, are suitable. The degree of oligomerization is a statistical average that is based on a homolog distribution that is usual for technical products of this kind. Products that are obtainable under the Plantacare® trademark include a glucosidically bound $C_8$ to $C_{16}$ alkyl group on each oligoglucoside residue whose average degree of oligomerization is 1 to 2, in particular 1.2 to 1.4. Particularly preferred $C_8$ to $C_{22}$ alkyl mono- and oligoglycosides are selected from octyl glucoside, decyl glucoside, lauryl glucoside, palmityl glucoside, isostearyl glucoside, stearyl glucoside, arachidyl glucoside, and behenyl glucoside, as well as mixtures thereof. The acyl glucamides derived from glucamine are also suitable as nonionic oil-in-water emulsifiers.

Ethoxylated sterols, in particular ethoxylated soy sterols, also represent oil-in-water emulsifiers suitable according to the present invention. The degree of ethoxylation must be greater than 5, preferably less than 10, in order to exhibit an HLB value greater than 7. Suitable commercial products are, for example, PEG-10 Soy Sterol, PEG-16 Soy Sterol, and PEG-25 Soy Sterol.

It is further preferred to use partial esters of polyglycerols having 2 to 10 glycerol units and esterified with 1 to 4 saturated or unsaturated, linear or branched, optionally hydroxylated $C_8$ to $C_{30}$ fatty acid esters, provided they have an HLB value of more than 7. Diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, and decaglycerol trihydroxystearate are particularly preferred.

Instead of or in addition to nonionic emulsifiers, ionic silicone-free emulsifiers can of course also be used. Cationic emulsifiers are particularly preferred here (see below).

Regardless of the nature of the silicone-free emulsifier, agents according to the present invention that include the silicone-free emulsifiers within narrower quantity ranges are preferred. These preferred agents are characterized in that they include, based on their weight, 0.02 to 4.5 wt. %, by preference 0.03 to 4.0 wt. %, more preferably 0.04 to 3.5 wt. %, even more preferably 0.05 to 3.0 wt. %, and in particular 0.1 to 1.0 wt. % of at least one silicone-free water-in-oil emulsifier.

As already mentioned, cationic compounds are particularly preferred as silicone-free emulsifiers. Agents according to the present invention that include exclusively cationic compounds as silicone-free emulsifiers are preferred here.

The agent can be provided with an antimicrobial effect, resp. its antimicrobial effect that may already be present as a result of other ingredients can be improved, by using quaternary surface-active compounds having an antimicrobial effect. QAVs suitable for this purposes are, for example, benzalkonium chloride (N-alkyl-N,N-dimethylbenzylammonium chloride, CAS No. 8001-54-5), Benzalkon B (m,p-dichlorobenzyldimethyl-$C_{12}$ alkylammonium chloride, CAS No. 58390-78-6), benzoxonium chloride (benzyldodecyl-bis-(2-hydroxyethyl)ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammoniumchlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5), and thiazoline iodide (CAS No. 15764-48-1), as well as mixtures thereof. Preferred QAVs are the benzalkonium chlorides having $C_8$ to $C_{18}$ alkyl residues, in particular $C_{12}$ to $C_{14}$ alkylbenzyldimethylammonium chloride. A particularly preferred QAV is cocopentaethoxymethylammonium methosulfate (INCI: PEG-5 Cocomonium Methosulfate; Rewoquat® CPEM).

Also included by preference as a cationic surfactant is at least one quaternary imidazoline compound, i.e. a compound that comprises a positively charged imidazoline ring. Formula I presented below shows the structure of these compounds:

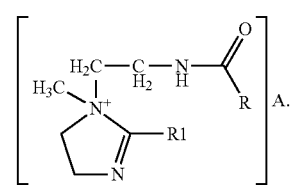

Formula I

The residues R and R1 each denote, mutually independently, a saturated or unsaturated, linear or branched hydrocarbon residue having a chain length from 8 to 30 carbon atoms. The preferred compounds of formula I include the same hydrocarbon residue for R and for R1. The chain length of residues R and R1 is preferably 12 carbon atoms. Compounds having a chain length of at least 16 carbon atoms are particularly preferred, and those having at least 20 carbon atoms are very particularly preferred. A highly preferred compound of formula I has a chain length of 21 carbon atoms. A product of this chain length is known, for example, by the designation Quaternium-91 or the commercial designations Crodazosoft® DBQ, which alongside Quaternium-91 further includes Cetrimonium Methosulfate and Cetearyl Alcohol, as well as Crodazosoft® SCQ, which alongside Quaternium-91 further includes PPG-3 Benzyl Ether Myristate. Examples that are particularly in accordance with the present invention are obtainable, for example, under the INCI names Quaternium-27, Quaternium-72, Quaternium-83, and Quaternium-91. It is most preferred to use the commercial products Crodazosoft® DBQ and Crodazosoft® SCQ, resp. Quaternium-91.

The imidazolines of formula I are included in the compositions according to the present invention in quantities from 0.01 to 20 wt. %, preferably in quantities from 0.05 to 10 wt. %, and very particularly preferably in quantities from 0.1 to 7.5 wt. %. The very best results are obtained in this context with quantities from 0.1 to 5 wt. %, based in each case on the total composition of the respective agent.

The following cationic surfactants in accordance with formula (Tkat-2) can furthermore be used:

RCO—X—N$^+$R$^1$R$^2$R$^3$A (Tkat-2).

R therein denotes a substituted or unsubstituted, branched or straight-chain alkyl or alkenyl residue having 11 to 35 carbon atoms in the chain, X denotes —O or —NR$^5$, R$^1$ denotes an alkylene group, having 2 to 6 carbon atoms, which can be substituted or unsubstituted; in the event of a substitution, substitution with an —OH or —NH group is preferred, R$^2$, R$^3$ each denote, mutually independently, an alkyl or hydroxyalkyl group having 1 to 6 carbon atoms in the chain, such that the chain can be straight or branched.

R5 denotes hydrogen or a C1 to C6 straight-chain or branched alkyl or alkenyl residue, which can also be substituted with a hydroxy group.

Within this structure class, the compounds having one of the following structures are used in preferred fashion:

CH$_3$(CH$_2$)$_{20}$CONH(CH$_2$)$_3$—N$^+$(CH$_3$)$_2$—CH$_2$CH$_3$A (Tkat-3)

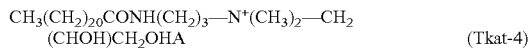

CH$_3$(CH$_2$)$_{20}$CONH(CH$_2$)$_3$—N$^+$(CH$_3$)$_2$—CH$_2$(CHOH)CH$_2$OHA (Tkat-4)

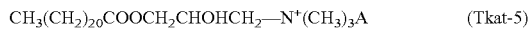

CH$_3$(CH$_2$)$_{20}$COOCH$_2$CHOHCH$_2$—N$^+$(CH$_3$)$_3$A (Tkat-5)

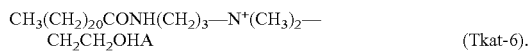

CH$_3$(CH$_2$)$_{20}$CONH(CH$_2$)$_3$—N$^+$(CH$_3$)$_2$—CH$_2$CH$_2$OHA (Tkat-6).

Examples of commercial products of this kind are Schercoquat BAS, Lexiquat AMG-BEO, Akypoquat 131, or Incroquat Behenyl HE.

In addition, esterquats in accordance with formula (Tkat1-2) can be used:

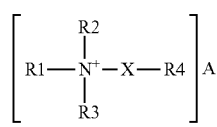

(Tkat1-2)

The residues R1, R2, and R3 therein are each mutually independent and can be the same or different. Residues R1, R2, and R3 denote:

a branched or unbranched alkyl residue having 1 to 4 carbon atoms, which can include at least one hydroxyl group, or a saturated or unsaturated, branched or unbranched, or a cyclic unsaturated or unsaturated alkyl residue having 6 to 30 carbon atoms, which can include at least one hydroxyl group, or an aryl or alkaryl residue, for example phenyl or benzyl, the residue (—X—R4), provided that at most two of the residues R1, R2, or R3 can denote this residue.

The residue —(X—R4) is included at least 1 to 3 times.

In this, X denotes:
1) —(CH2)$_n$—, where n=1 to 20, by preference n=1 to 10, and particularly preferably n=1 to 5, or
2) —(CH$_2$—CHR5-O)$_n$—, where n=1 to 200, by preference 1 to 100, particularly preferably 1 to 50, and particularly preferably 1 to 20, where R5 has the meaning of hydrogen, methyl, or ethyl, and R4 denotes:
1) R6-O—CO—, in which R6 is a saturated or unsaturated, branched or unbranched, or a cyclic saturated or unsaturated alkyl residue having 6 to 30 carbon atoms, which can include at least one hydroxy group, and which if applicable can be further oxyethylated with 1 to 100 ethylene oxide units and/or 1 to 100 propylene oxide units, or
2) R7-CO—, in which R7 is a saturated or unsaturated, branched or unbranched, or a cyclic saturated or unsaturated alkyl residue having 6 to 30 carbon atoms, which can include at least one hydroxy group, and which optionally can be further oxyethylated with 1 to 100 ethylene oxide units and/or 1 to 100 propylene oxide units, and A denotes a physiologically acceptable organic or inorganic anion.

Such products are marketed, for example, under the trademarks Rewoquat®, Stepantex®, Dehyquart®, and Armocare®. Examples of such esterquats are the products Armocare® VGH-70—an N,N-bis(2-palmitoyloxyethyl)dimethylammonium chloride—as well as Dehyquart® F-75, Dehyquart® C-4046, Dehyquart® L-80, Dehyquart® F-30, Dehyquart® AU-35, Rewoquat® WE18, Rewoquat® WE38 DPG, and Stepantex® VS 90.

Further compounds of formula (Tkat1-2) that are particularly preferred according to the present invention belong to formula (Tkat1-2.1), the cationic betaine esters:

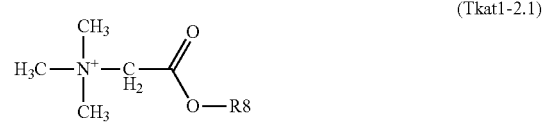

(Tkat1-2.1)

The meaning of R8 corresponds to that of R7.

Monoalkyltrimethylammonium salts having an alkyl residue chain length from 16 to 24 carbon atoms can be included as a further ingredient.

These compounds have the structure depicted in formula (Tkat1-1):

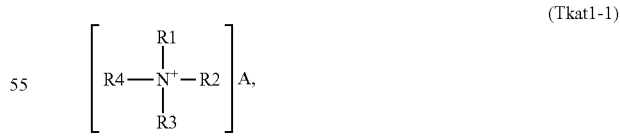

(Tkat1-1)

in which R1, R2, and R3 each denote a methyl group and R4 denotes a saturated, branched or unbranched alkyl residue having a chain length from 16 to 24 carbon atoms.

Examples of compounds of formula (Tkat1-1) are cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide, and behenyltrimethylammonium methosulfate.

In a particularly preferred embodiment of the invention, the agents according to the present invention further include at least one amine and/or cationized amine, in particular an amidoamine and/or cationized amidoamine, having the following structural formulas:

    (Tkat7) and/or

    (Tkat8)

in which

R1 denotes an acyl or alkyl residue having 6 to 30 carbon atoms, which can be branched or unbranched, saturated or unsaturated, and such that the acyl residue and/or alkyl residue can include at least one OH group, and R2, R3, and R4 each denote, mutually independently, hydrogen or an alkyl residue having 1 to 4 carbon atoms, which can be the same or different, saturated or unsaturated, and A signifies an anion, and n signifies a whole number between 1 and 10.

Also preferred are those amidoamines and/or quaternized amidoamines in which R2, R3, and/or R4 in formulas (Tkat7) and/or (Tkat8) signify a residue in accordance with the general formula $CH_2CH_2OR5$ in which R5 can have the meaning of alkyl residues having 1 to 4 carbon atoms, hydroxyethyl, or hydrogen. The preferred value of n in the general formulas (Tkat7) and/or (Tkat8) is a whole number between 2 and 5.

Also preferred are those amidoamines ad/or quaternized amidoamines in which R2, R3, and/or R4 in formulas (Tkat7) and/or (Tkat8) signify a residue in accordance with the general formula CH2CH2OR5 in which R5 can have the meaning of alkyl residues having 1 to 4 carbon atoms, hydroxyethyl, or hydrogen. The preferred value of n in the general formulas (Tkat7) and/or (Tkat8) is a whole number between 2 and 5.

The alkyl residue having 1 to 4 carbon atoms of R2, R3, and R4 in the general formula (Tkat7) and/or (Tkat8), can include at least one hydroxyl group.

The alkylamidoamines both can be present as such, and can be converted by protonation in a corresponding acid solution into a quaternary compound in the composition. The cationic alkylamidoamines are preferred according to the present invention.

The following, for example, are appropriate as amidoamines to be used according to the present invention, which optionally can be quaternized: Witcamine 100 (Witco, INCI name. Cocamidopropyl Dimethylamine), Incromine BB (Croda, INCI name: Behenamidopropyl Dimethylamine), Mackine 401 (McIntyre, INCI name: Isostearylamidopropyl Dimethylamine) and other Mackine grades, Adogen S18V (Witco, INCI name: Stearylamidopropyl Dimethylamine) and, as permanently cationic aminoamines: Rewoquat® 50 (Witco Surfactants GmbH, INCI name: Ricinoleamidopropyltrimonium Methosulfate), Empigen CSC (Albright & Wilson, INCI name: Cocamidopropyltrimonium Chloride), Swanol Lanoquat DES-50 (Nikko, INCI name: Quaternium-33), Rewoquat UTM 50 (Witco Surfactants GmbH, Undecyleneamidopropyltrimonium Methosulfate).

The anion A in accordance with all the structural formulas presented above of all the cationic compounds presented above is selected from the physiologically acceptable anions. Examples thereof that may be recited are the halide ions, fluoride, chloride, bromide, sulfate of the general formula $RSO_3^-$ in which R has the meaning of a saturated or unsaturated alkyl residues having 1 to 4 carbon atoms, or anionic residues of organic acids such as maleate, fumarate, oxalate, tartrate, citrate, lactate, or acetate.

The aforementioned cationic surfactants can be used individually or in any combination with one another, quantities between 0.01 and 20 wt. %, preferably quantities from 0.01 to 10 wt. %, and very particularly quantities from 0.1 to 7.5 wt. % being included. The best results of all are obtained with quantities from 0.1 to 5 wt. %, based in each case on the total composition of the respective agent.

Very particularly preferred agents according to the present invention are characterized in that they include as silicone-free emulsifiers at least one cationic surfactant, by preference at least one imidazolinium salt or at least one $C_{8-24}$ alkyltrimethylammonium salt, which particularly preferably include a $C_{10-20}$ alkyltrimethylammonium salt and more preferably $C_{12-18}$ alkyltrimethylammonium salts, and in particular cetyltrimethylammonium chloride, or a mixture of at least one imidazolinium salt and a $C_{8-24}$ alkyltrimethylammonium salt.

Cationized protein hydrolysates are further to be included among the obligatory ingredients as component d) according to Claim 1, in which context the underlying protein hydrolysate can derive from animals, for example from collagen, milk, or keratin, from plants, for example from wheat, corn, rice, potatoes, soy, moringa, or almonds, from marine life forms, for example from fish collagen or algae, or from biotechnologically obtained protein hydrolysates. Those cationic protein hydrolysates whose underlying protein component has a molecular weight from 100 to 25,000 dalton, preferably 250 to 5,000 dalton, highly preferably 250 to 1000 dalton, are preferred. Also to be understood as cationic protein hydrolysates are quaternized amino acids and mixtures thereof. Quaternization of the protein hydrolysates or of the amino acids is often carried out by means of quaternary ammonium salts such as, for example, N,N-dimethyl-N-(n-alkyl)-N-(2-hydroxy-3-chloro-n-propyl)ammonium halides. Typical examples that may be mentioned of cationic protein hydrolysates and derivatives according to the present invention are the products listed under the INCI names in the "International Cosmetic Ingredient Dictionary and Handbook," (seventh edition 1997, The Cosmetic, Toiletry, and Fragrance Association, 1101 17$^{th}$ Street, N.W., Suite 300, Washington, D.C. 20036-4702), and available commercially: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-Hydrolyzed Collagen, Quaternium-79 Hydrolyzed Keratin, Quaternium-79 Hydrolyzed Milk Protein, Quaternium-79 Hydrolyzed Soy Protein, Quaternium-79 Hydrolyzed Wheat Protein.

The plant-based cationic protein hydrolysates and derivates are very particularly preferred, and those based on wheat, rice, corn, soy, almond, or moring a are highly preferred. It is highly preferred to use cationic protein hydrolysates based on wheat. The commercial products Gluadin® WQ, Gluadin® WQT, the products of the Hydrotriticum® series of the Croda company are examples of these highly preferred cationic protein hydrolysates.

The cationic protein hydrolysates are included in the compositions according to the present invention preferably in quantities from 0.1 to 5.0 wt. %, based on the total agent. Quantities from 0.1 to 3 wt. % are particularly preferred.

By way of the selection of the nature and quantity of the silicone-including and silicone-free emulsifiers, and their ratio to cyclodimethicone and to any oily substances that may be included in the agent, the agents according to the present invention can be formulated as a stable emulsion especially in the presence of the cationic protein hydrolysates. It is, however, also possible and highly preferred to provide the agents according to the present invention in the form of an emulsion that is at least partly unstable. The result is to provide a two-phase product that includes a lower aqueous phase and an upper oil phase. If the emulsion does not completely break, a two-phase product forms which includes a clear aqueous lower phase and a milky/cloudy upper phase made of unbroken emulsion. Such products possess a high level of optical differentiation, and high consumer acceptance. The consumer shakes the product before use and applies the (briefly stable) emulsion onto the hair, while the rest of the emulsion in the product package separates again. The briefly stable emulsion should be stable for a period of time from a few seconds to at most 10 minutes. After utilization, the two-phase state should become re-established within a few minutes, so that the consumer recognizes that he or she may need to homogenize the product again, by shaking, before using it again. As already described previously, it is precisely during shaking in order to create the one-phase state that large shear forces occur, which can result in instabilities of the entire product. These instabilities occur in the existing art. The present invention avoids these instabilities, in the context of short-term homogenization caused by shaking by the consumer, by using cationic protein hydrolysates. Two-phase products according to the present invention are particularly preferred for these reasons.

The care-providing effects of the agents according to the present invention can be even further enhanced by selection of a suitable pH for the agents according to the present invention. Acid agents according to the present invention, in particular, exhibit extraordinarily good care-providing properties without weighing the hairstyle. Agents preferred according to the present invention are therefore characterized in that they have a pH of less than 5, by preference less than 4, more preferably from 2.5 to 3.5, and in particular from 2.7 to 3.3.

As a further optional constituent, the agents according to the present invention can include 0.01 to 10 wt. % of at least one polymer from the group of the cationic and/or amphoteric polymers.

The cationic polymers can be homo- or copolymers, the quaternary nitrogen groups being included either in the polymer chain or, by preference, as a substituent on one or more of the monomers. The ammonium-group-including monomers can be copolymerized with non-cationic monomers. Suitable cationic monomers are unsaturated, radically polymerizable compounds that carry at least one cationic group, in particular ammonium-substituted vinyl monomers such as, for example, trialkylmethacryloxyalkylammonium, trialkylacryloxyalkylammonium, dialkyldiallylammonium, and quaternary vinylammonium monomers having cyclic groups including cationic nitrogens, such as pyridinium, imidazolium, or quaternary pyrrolidones, e.g. alkylvinylimidazolium, alkylvinylpyridinium, or alkyvinylpyrollidone salts. The alkyl groups of these monomers are by preference lower alkyl groups such as, for example, C1 to C7 alkyl groups, particularly preferably C1 to C3 alkyl groups.

The ammonium-group-including monomers can be copolymerized with non-cationic monomers. Suitable comonomers are, for example, acrylamide, methacrylamide; alkyl and dialkylacrylamide, alkyl and dialkylmethacrylamide, alkyl acrylate, alkyl methacrylate, vinylcaprolactone, vinylcaprolactam, vinylpyrrolidone, vinyl esters, e.g. vinyl acetate, vinyl alcohol, propylene glycol, or ethylene glycol, the alkyl groups of these monomers being by preference C1 to C7 alkyl groups, particularly preferably C1 to C3 alkyl groups.

Suitable polymers having quaternary amine groups are, for example, the polymers described in the CTFA Cosmetic Ingredient Dictionary under the "Polyquaternium" designations, such as methylvinylimidazolium chloride/vinylpyrrolidone copolymer (Polyquaternium-16), or quaternized vinylpyrrolidone/dimethylaminoethyl methacrylate copolymer (Polyquaternium-11).

Suitable among the cationic polymers that can be included in the agent according to the present invention is, for example, the vinylpyrrolidone/dimethylaminoethyl methacrylate methosulfate copolymer that is marketed under the commercial names Gafquat® 755 N and Gafquat® 734 by the GAF company, USA, and of which Gafquat® 734 is particularly suitable. Further cationic polymers are, for example, the copolymer of polyvinylpyrrolidone and imidazolimine methochloride marketed by BASF, Germany, under the trade name Luviquat® HM 550, the terpolymer of dimethyldiallylammonium chloride, sodium acrylate, and acrylamide marketed by the Calgon company, USA, under the trade name Merquat® Plus 3300, and the vinylpyrrolidone/methacrylamidopropyltrimethylammonium chloride copolymer marketed by the ISP company under the trade name Gafquat® HS 100.

Homopolymers of the general formula (P1),

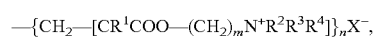

in which $R^1$=—H or —$CH_3$, $R^2$, $R^3$ and $R^4$ are selected, mutually independently, from C1-4 alkyl, alkenyl, or hydroxyalkyl groups, m=1, 2, 3 or 4, n is a natural number, and $X^-$ is a physiologically acceptable organic or inorganic anion. In the context of these polymers, the ones preferred according to the present invention are those for which at least one of the following conditions applies: $R^1$ denotes a methyl group, $R^2$, $R^3$, and $R^4$ denote methyl groups, m has the value 2.

Possibilities as physiologically acceptable counter ions X— are, for example, halide ions, sulfate ions, phosphate ions, methosulfate ions, and organic ions such as lactate, citrate, tartrate, and acetate ions. Halide ions, in particular chloride, are preferred.

A particularly suitable homopolymer is the poly(methacryloyloxyethyltrimethylammonium chloride) (crosslinked, if desired) having the INCI name Polyquaternium-37. Such products are available commercially, for example, under the designations Rheocare® CTH (Cosmetic Rheologies) and Synthalen® CR (3V Sigma).

The homopolymer is preferably used in the form of a nonaqueous polymer dispersion. Such polymer dispersions are obtainable commercially under the designations Salcare® SC 95 and Salcare® SC 96.

A copolymer preferred according to the present invention is the crosslinked copolymer of acrylamide and methacryloyloxyethyltrimethylammonium chloride. Such copolymers are commercially obtainable under the designation Salcare® SC 92.

Suitable cationic polymers that are derived from natural polymers are cationic derivatives of polysaccharides, for example cationic derivatives of cellulose, starch, or guar. Chitosan and chitosan derivatives are also suitable. Cationic polysaccharides have the general formula (P-3)

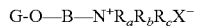

$$G\text{-}O\text{-}B\text{-}N^+R_aR_bR_cX^-$$

G is an anhydroglucose residue, for example starch or cellulose anhydroglucose,

B is a divalent connecting group, for example alkylene, oxyalkylene, polyoxyalkylene, or hydroxyalkylene, $R_a$, $R_b$ and $R_c$ are, mutually independently, alkyl, aryl, alkylaryl, arylalkyl, alkoxyalkyl, or alkoxyaryl each having up to 18 carbon atoms, the total number of carbon atoms in $R_a$, $R_b$, and $R_c$ by preference being a maximum of 20, $X^-$ is a usual counter anion and is by preference chloride.

A cationic cellulose is marketed by Amerchol under the designation Polymer JR® 400 and has the INCI name Polyquaternium-10. A further cationic cellulose bears the INCI name Polyquaternium-24 and is marketed under the trade name Polymer LM-200 by Amerchol. Further commercial products are the compounds Celquat® H 100 and Celquat® L 200. The aforesaid commercial products are preferred cationic celluloses. Further preferred cationic celluloses are known by the INCI names Polyquaternium-67 and Polyquaternium-72.

Suitable cationic guar derivatives are marketed under the commercial designation Jaguar® and have the INCI name Guar Hydroxypropyltrimonium Chloride. Particularly suitable cationic guar derivatives are additionally available commercially from the Hercules company under the designation N-Hance®. Further cationic guar derivatives are marketed by the Cognis company under the designation Cosmedia®. A preferred cationic guar derivative is the commercial product AquaCat® of the Hercules company. This raw material is a cationic guar derivative that is already predissolved.

A suitable chitosan is marketed, for example, by the Kyowa Oil & Fat company, Japan, under the trade name Flonac®. A preferred chitosan salt is chitosonium pyrrolidonecarboxylate, which is marketed e.g. under the designation Kytamer® PC by the Amerchol company, USA. Further chitosan derivatives are readily available commercially under the commercial designations Hydagen® CMF, Hydagen® HCMF, and Chitolam® NB/101.

Further preferred cationic polymers are, for example:
cationic alkyl polyglycosides,
cationized honey, for example the commercial product Honeyquat® 50,
polymeric dimethyldiallylammonium salts and copolymers thereof with esters and amides of acrylic acid and methacrylic acid. The products available commercially under the designations Merquat® 100 (poly(dimethyldiallylammonium chloride)) and Merquat® 550 (dimethyldiallylammonium chloride/acrylamide copolymer) are examples of such cationic polymers,
vinylpyrrolidone/vinylimidazolium methochloride copolymers, such as those offered under the designations Luviquat® FC 370, FC 550, FC 905, and HM 552, quaternized poly(vinyl alcohol),
and the polymers known under the names Polyquaternium-2, Polyquaternium-17, Polyquaternium-18, and Polyquaternium-27, having quaternary nitrogen atoms in the main polymer chain,
vinylpyrrolidone/vinylcaprolactam/acrylate terpolymers such as those having acrylic acid esters and acrylic acid amides as a third monomer module, and offered commercially e.g. under the designation Aquaflex® SF 40.

Also usable according to the present invention are the copolymers of vinylpyrrolidone such as those obtainable as the commercial products Copolymer 845 (manufacturer: ISP), Gaffix® VC 713 (manufacturer: ISP), Gafquat® ASCP 1011, Gafquat® HS 110, Luviquat® 8155, and Luviquat® MS 370.

The cationic polymers are included in the compositions according to the present invention preferably in quantities from 0.01 to 10 wt. %, based on the total agent. Quantities from 0.05 to 5 wt. % are particularly preferred.

Regardless of whether or not amphoteric polymers are included in the agents, further preferred agents according to the present invention are characterized in that they include, based on their weight, 0.05 to 7.5 wt. %, by preference 0.1 to 5 wt. %, particularly preferably 0.2 to 3.5 wt. %, and in particular 0.25 to 2.5 wt. % cationic polymer(s).

In summary, agents according to the present invention that include based on their weight, 0.05 to 7.5 wt. %, by preference 0.1 to 5 wt. %, particularly preferably 0.2 to 3.5 wt. %, and in particular 0.25 to 2.5 wt. % cationic polymer(s) are preferred, preferred cationic polymer(s) being selected from
poly(methacryloyloxyethyltrimethylammonium chloride) (INCI: Polyquaternium-37), and/or
quaternized cellulose derivatives (INCI: Polyquaternium-10), and/or
cationic alkylpolyglycosides, and/or
cationized honey, and/or
cationic guar derivatives, and/or
polymeric dimethyldiallylammonium salts and copolymers thereof with esters and amides of acrylic acid and methacrylic acid, and/or
copolymers of vinylpyrrolidone with quaternized derivatives of dialkylaminoalkyl acrylate and methacrylate, and/or
vinylpyrrolidone-vinylimidazolium methochloride copolymers, and/or
quaternized polyvinyl alcohol, and/or
Polyquaternium-2, and/or
Polyquaternium-7, and/or
Polyquaternium-16, and/or
Polyquaternium-17, and/or
Polyquaternium-18, and/or
Polyquaternium-24, and/or
Polyquaternium-27.

Amphoteric polymers can also be used as polymers. The term "amphoteric polymers" encompasses both those polymers that include in the molecule both free amino groups and free —COOH or —SO₃H groups and are capable of forming internal salts, and zwitterionic polymers, which include quaternary ammonium groups and —COO⁻ or —SO₃⁻ groups in the molecule, and those polymers that include —COOH or —SO₃H groups and quaternary ammonium groups.

Amphoteric and/or cationic polymers that are preferred according to the present invention are those polymerizates in which a cationic group derives from at least one of the following monomers:

i) monomers having quaternary ammonium groups of the general formula (Mono1)

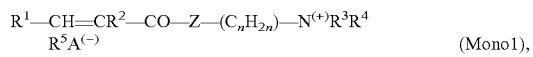

in which $R^1$ and $R^2$, mutually independently, denote hydrogen or a methyl group and $R^3$, $R^4$, and $R^5$, mutually independently, denote alkyl groups having 1 to 4 carbon atoms, Z denotes an NH group or an oxygen atom, n is a whole number from 2 to 5, and $A^{(-)}$ is the anion of an organic or inorganic acid, ii) monomers having quaternary ammonium groups of the general formula (Mono2)

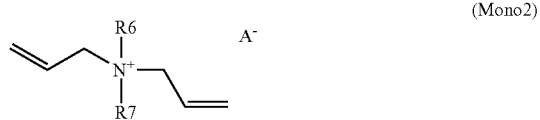

in which $R^6$ and $R^7$, mutually independently, denote a ($C_1$ to $C_4$) alkyl group, in particular a methyl group, and $A^-$ is the anion of an organic or inorganic acid, iii) monomeric carboxylic acids of the general formula (Mono3):

in which $R^8$ and $R^9$, mutually independently, are hydrogen or methyl groups.

Those polymerizates in which the monomers used are of type (i) in which $R^3$, $R^4$, and $R^5$ are methyl groups, Z is an NH group, and $A^{(-)}$ is a halide, methoxysulfate, or ethoxysulfate ion, are particularly preferred; acrylamidopropyltrimethylammonium chloride is a particularly preferred monomer (i). Acrylic acid is preferably utilized as monomer (ii) for the aforesaid polymerizates.

Particularly preferred amphoteric polymers are copolymers of at least one monomer (Mono1) resp. (Mono2) with the monomer (Mono3), in particular copolymers of monomers (Mono2) and (Mono3). Amphoteric polymers used very particularly preferably according to the present invention are copolymerizates of diallyldimethylammonium chloride and acrylic acid. These copolymerizates are marketed under the INCI name Polyquaternium-22, inter alia with the commercial name Merquat® 280 (Nalco).

Furthermore, the amphoteric polymers according to the present invention can additionally include, alongside a monomer (Mono1) or (Mono2) and a monomer (Mono3), a monomer (Mono4)

iv) monomeric carboxylic acid amides of the general formula (Mono4),

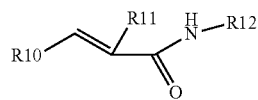

in which $R^{10}$ and $R^{11}$, mutually independently, are hydrogen or methyl groups, and $R^{12}$ denotes a hydrogen atom or a ($C_1$ to $C_8$) alkyl group.

Amphoteric polymers based on a comonomer (Mono4) that are used very particularly preferably according to the present invention are terpolymers of diallyldimethylammonium chloride, acrylamide, and acrylic acid. These copolymerizates are marketed under the INCI name Polyquaternium-39, inter alia with the commercial name Merquat® Plus 3330 (Nalco).

The amphoteric polymers can in general be used according to the present invention both directly and in a salt form that is obtained by neutralizing the polymerizates, for example with an alkali hydroxide.

With particular preference, the amphoteric polymers used in the agents according to the present invention include monomers from the group of the acrylamides and/or methacrylamides having alkylammonium groups. Acrylic acid and/or methacrylic acid and/or crotonic acid and/or 2-methylcrotonic acid have proven successful as monomers, having anionic groups, that are additionally included in the polymers.

In summary, preferred agents according to the present invention are those in which the amphoteric polymer(s) are copolymerizates of at least one of the monomers
    trimethylammonium ethyl acrylamide and/or
    trimethylammonium ethyl methacrylamide and/or
    trimethylammonium propyl acrylamide and/or
    trimethylammonium propyl methacrylamide and/or
    trimethylammonium ethyl acrylamide and/or
    trimethylammonium ethyl acrylate and/or
    trimethylammonium ethyl methacrylate and/or
    trimethylammonium ethyl acrylate and/or
    ethyldimethylammonium ethyl acrylamide and/or
    ethyldimethylammonium ethyl methacrylamide and/or
    ethyldimethylammonium propyl acrylamide and/or
    ethyldimethylammonium propyl methacrylamide and/or
    ethyldimethylammonium ethyl acrylamide and/or
    ethyldimethylammonium ethyl acrylate and/or
    ethyldimethylammonium ethyl methacrylate and/or
    ethyldimethylammonium ethyl acrylate
with at least one of the monomers
    acrylic acid and/or
    methacrylic acid and/or
    crotonic acid and/or
    2-methylcrotononic acid.

Amphoteric polymers particularly preferred according to the present invention are:
    copolymers of trimethylammonium ethyl acrylamide with acrylic acid
    copolymers of trimethylammonium ethyl acrylamide with methacrylic acid
    copolymers of trimethylammonium ethyl acrylamide with crotonic acid
    copolymers of trimethylammonium ethyl acrylamide with 2-methylcrotonic acid
    copolymers of trimethylammonium ethyl methacrylamide with acrylic acid
    copolymers of trimethylammonium ethyl methacrylamide with methacrylic acid copolymers of trimethylammonium ethyl methacrylamide with crotonic acid
copolymers of trimethylammonium ethyl methacrylamide with 2-methylcrotonic acid
copolymers of trimethylammonium propyl acrylamide with acrylic acid
copolymers of trimethylammonium propyl acrylamide with methacrylic acid
copolymers of trimethylammonium propyl acrylamide with crotonic acid
copolymers of trimethylammonium propyl acrylamide with 2-methylcrotonic acid
copolymers of trimethylammonium propyl methacrylamide with acrylic acid
copolymers of trimethylammonium propyl methacrylamide with methacrylic acid
copolymers of trimethylammonium propyl methacrylamide with crotonic acid
copolymers of trimethylammonium propyl methacrylamide with 2-methylcrotonic acid
copolymers of trimethylammonium ethyl acrylamide with acrylic acid
copolymers of trimethylammonium ethyl acrylamide with methacrylic acid
copolymers of trimethylammonium ethyl acrylamide with crotonic acid
copolymers of trimethylammonium ethyl acrylamide with 2-methylcrotonic acid
copolymers of trimethylammonium ethyl acrylate with acrylic acid
copolymers of trimethylammonium ethyl acrylate with methacrylic acid
copolymers of trimethylammonium ethyl acrylate with crotonic acid
copolymers of trimethylammonium ethyl acrylate with 2-methylcrotonic acid
copolymers of trimethylammonium ethyl methacrylate with acrylic acid
copolymers of trimethylammonium ethyl methacrylate with methacrylic acid
copolymers of trimethylammonium ethyl methacrylate with crotonic acid
copolymers of trimethylammonium ethyl methacrylate with 2-methylcrotonic acid
copolymers of trimethylammonium ethyl acrylate with acrylic acid
copolymers of trimethylammonium ethyl acrylate with methacrylic acid
copolymers of trimethylammonium ethyl acrylate with crotonic acid
copolymers of trimethylammonium ethyl acrylate with 2-methylcrotonic acid
copolymers of ethyldimethylammonium ethyl acrylamide with acrylic acid
copolymers of ethyldimethylammonium ethyl acrylamide with methacrylic acid
copolymers of ethyldimethylammonium ethyl acrylamide with crotonic acid
copolymers of ethyldimethylammonium ethyl acrylamide with 2-methylcrotonic acid
copolymers of ethyldimethylammonium ethyl methacrylamide with acrylic acid
copolymers of ethyldimethylammonium ethyl methacrylamide with methacrylic acid
copolymers of ethyldimethylammonium ethyl methacrylamide with crotonic acid
copolymers of ethyldimethylammonium ethyl methacrylamide with 2-methylcrotonic acid
copolymers of ethyldimethylammonium propyl acrylamide with acrylic acid
copolymers of ethyldimethylammonium propyl acrylamide with methacrylic acid
copolymers of ethyldimethylammonium propyl acrylamide with crotonic acid
copolymers of ethyldimethylammonium propyl acrylamide with 2-methylcrotonic acid
copolymers of ethyldimethylammonium propyl methacrylamide with acrylic acid
copolymers of ethyldimethylammonium propyl methacrylamide with methacrylic acid
copolymers of ethyldimethylammonium propyl methacrylamide with crotonic acid
copolymers of ethyldimethylammonium propyl methacrylamide with 2-methylcrotonic acid
copolymers of ethyldimethylammonium ethyl acrylamide with acrylic acid
copolymers of ethyldimethylammonium ethyl acrylamide with methacrylic acid
copolymers of ethyldimethylammonium ethyl acrylamide with crotonic acid
copolymers of ethyldimethylammonium ethyl acrylamide with 2-methylcrotonic acid
copolymers of ethyldimethylammonium ethyl acrylate with acrylic acid
copolymers of ethyldimethylammonium ethyl acrylate with methacrylic acid
copolymers of ethyldimethylammonium ethyl acrylate with crotonic acid
copolymers of ethyldimethylammonium ethyl acrylate with 2-methylcrotonic acid
copolymers of ethyldimethylammonium ethyl methacrylate with acrylic acid
copolymers of ethyldimethylammonium ethyl methacrylate with methacrylic acid
copolymers of ethyldimethylammonium ethyl methacrylate with crotonic acid
copolymers of ethyldimethylammonium ethyl methacrylate with 2-methylcrotonic acid
copolymers of ethyldimethylammonium ethyl acrylate with acrylic acid
copolymers of ethyldimethylammonium ethyl acrylate with methacrylic acid
copolymers of ethyldimethylammonium ethyl acrylate with crotonic acid
copolymers of ethyldimethylammonium ethyl acrylate with 2-methylcrotonic acid.

The amphoteric polymer(s) is/are used by preference within narrower quantity ranges. For example, agents according to the present invention that include, based on their weight, 0.05 to 7.5 wt. %, by preference 0.1 to 5 wt. %, particularly preferably 0.2 to 3.5 wt. %, and in particular 0.25 to 2.5 wt. % amphoteric polymer(s), are preferred.

The anionic polymers are anionic polymers that comprise carboxylate and/or sulfonate groups. Examples of anionic monomers of which such polymers can be made up are acrylic acid, methacrylic acid, crotonic acid, maleic acid anhydride, and 2-acrylamido-2-methylpropanesulfonic acid. The acid groups can be present entirely or partially as a sodium, potassium, ammonium, mono- or triethanolammonium salt. Preferred monomers are 2-acrylamido-2-methylpropanesulfonic acid and acrylic acid.

Anionic polymers that include 2-acrylamido-2-methylpropanesulfonic acid as a sole monomer or co-monomer have proven to be very particularly effective, in which context the sulfonic acid group can be present entirely or partially as a sodium, potassium, ammonium, mono- or triethanolammonium salt.

The homopolymer of 2-acrylamido-2-methylpropanesulfonic acid that is available commercially, for example under the designation Rheothik® 11-80, is particularly preferred.

Within this embodiment, it may be preferred to use copolymers of at least one anionic monomer and at least one nonionogenic monomer. With regard to the anionic monomers, reference is made to the substances listed above. Preferred nonionogenic monomers are acrylamide, methacrylamide, acrylic acid esters, methacrylic acid esters, vinylpyrrolidone, vinyl ethers, and vinyl esters.

Preferred anionic copolymers are acrylic acid/acrylamide copolymers and in particular polyacrylamide copolymers with sulfonic acid group-including monomers. One such polymer is included in the commercial product Sepigel® 305 of the SEPPIC company.

The sodium acryloyl dimethyl taurate copolymers marketed, under the designation Simulgel® 600, as a compound with isohexadecane and polysorbate-80 have also proven particularly effective according to the present invention.

Similarly preferred anionic homopolymers are uncrosslinked and crosslinked polyacrylic acids. Allyl ethers of pentaerythritol, of sucrose, and of propylene can be preferred crosslinking agents. Such compounds are obtainable commercially, for example, under the trademark Carbopol®.

Copolymers of maleic acid anhydride and methylvinyl ether, in particular those having crosslinks, are also color-preserving polymers. A maleic acid/methylvinyl ether copolymer crosslinked with 1,9-decadiene is obtainable commercially under the designation Stabileze® QM.

The anionic polymers are included in the agents according to the present invention preferably in quantities from 0.05 to 10 wt. %, based on the total agent. Quantities from 0.1 to 5 wt. % are particularly preferred.

A polyurethane that is very particularly preferred according to the present invention is on the market under the commercial designation Luviset® PUR (BASF).

In a further embodiment, the agents according to the present invention can include nonionogenic polymers.

Suitable nonionogenic polymers are, for example:

Vinylpyrrolidone/vinyl ester copolymers such as those marketed, for example, under the trademark Luviskol® (BASF). Luviskol® VA 64 and Luviskol® VA 73, which are each vinylpyrrolidone/vinyl acetate copolymers, are likewise preferred nonionic polymers.

Cellulose ethers, such as hydroxypropyl cellulose, hydroxyethyl cellulose, and methylhydroxypropyl cellulose, such as those marketed, for example, under the trademarks Culminal® and Benecel® (AQUALON) and Natrosol® grades (Hercules).

Starch and derivatives thereof, in particular starch ethers, for example Structure® XL (National Starch), a multifunctional, salt-tolerant starch, shellac, polyvinylpyrrolidones such as those marketed, for example, under the designation Luviskol® (BASF).

The nonionic polymers are included in the compositions according to the present invention preferably in quantities from 0.05 to 10 wt. %, based on the total agent. Quantities from 0.1 to 5 wt. % are particularly preferred.

It is also possible according to the present invention for the preparations used to include multiple, in particular two, different polymers of identical charge and/or one ionic and one amphoteric and/or nonionic polymer.

In a further preferred embodiment of the invention, the effect of the active substance according to the present invention can be further optimized by means of fatty substances. "Fatty substances" are to be understood as fatty acids, fatty alcohols, natural and synthetic waxes, which can be present both in solid form and in liquid form in aqueous dispersion, and natural and synthetic cosmetic oil components.

The fatty acids that can be used are linear and/or branched, saturated and/or unsaturated fatty acids having 6 to 30 carbon atoms. Fatty acids having 10 to 22 carbon atoms are preferred. Among those that might be mentioned are, for example, the isostearic acids, such as the commercial products Emersol® 871 and Emersol® 875, and isopalmitic acids such as the commercial product Edenor® IP 95, as well as all other fatty acids marketed under the Edenor® commercial designations (Cognis). Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid, as well as industrial mixtures thereof that occur, for example, upon high-pressure cleavage of natural fats and oils, upon oxidation of aldehydes from Roelen oxo-synthesis, or upon dimerization of unsaturated fatty acids. The fatty acid cuts that are obtainable from coconut oil or palm oil are usually particularly preferred; the use of stearic acid is, as a rule, particularly preferred.

The quantity used is 0.1 to 15 wt. % based on the total agent. In a preferred embodiment, the quantity is preferably 0.5 to 10 wt. %, and quantities from 1 to 5 wt. % are very particularly advantageous.

Fatty alcohols that can be used are saturated, mono- or polyunsaturated, branched or unbranched fatty alcohols having $C_6$ to $C_{30}$, preferably $C_{10}$ to $C_{22}$, and very particularly preferably $C_{12}$ to $C_{22}$ carbon atoms. Usable in the context of the invention are, for example, decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, caprinyl alcohol, linoleyl alcohol, linolenyl alcohol, and behenyl alcohol, as well as Guerbet alcohols thereof, this listing being intended to be exemplary and not limiting in nature. The fatty alcohols derive, however, from preferably natural fatty acids; it is usually possible to proceed from an extraction from the esters of the fatty acids by reduction. Also usable according to the present invention are those fatty alcohol cuts that are generated by the reduction of naturally occurring triglycerides such as beef tallow, palm oil, peanut oil, colza oil, cottonseed oil, soybean oil, sunflower oil, and linseed oil, or from fatty acid esters resulting from transesterification products thereof with corresponding alcohols, and thus represent a mixture of different fatty alcohols. Such substances are, for example, available commercially under the designations Stenol®, e.g. Stenol® 1618, or Lanette®, e.g. Lanette® 0, or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16 Isofol® 24, Isofol® 36, Isocarb® 12, Isocarb® 16, or Isocarb® 24. It is of course also possible according to the present invention to use wool-wax alcohols such as those available commercially under the designations Corona®, White Swan®, Coronet®, or Fluilan®. The fatty alcohols are used in quantities from 0.1 to 20 wt. % based on the total preparation, preferably in quantities from 0.1 to 10 wt. %.

Natural or synthetic waxes that can be used according to the present invention are solid paraffins or isoparaffins, carnauba waxes, beeswaxes, candelilla waxes, ozocerites, ceresin, spermaceti, sunflower wax, fruit waxes such as, for example, apple wax or citrus wax, or microcrystalline waxes made from PE or PP. Such waxes are obtainable, for example, via Kahl & Co., Trittau.

Among the natural and synthetic cosmetic oily substances that can enhance the effect of the active substance according to the present invention may be listed, for example:

Vegetable oils. Examples of such oils are sunflower oil, olive oil, soybean oil, rapeseed oil, almond oil, jojoba oil, orange oil, wheat germ oil, peach-kernel oil, and the liquid components of coconut oil. Also suitable, however, are other triglyceride oils such as the liquid components of beef tallow, as well as synthetic triglyceride oils.

Liquid paraffin oils, isoparaffin oils, and synthetic hydrocarbons, as well as di-n-alkyl ethers having a total of between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether, and n-hexyl-n-undecyl ether, as well as ditertbutyl ether, diisopentyl ether, di-3-ethyldecyl ether, tert-butyl-n-octyl ether, isopentyl-n-octyl ether, and 2-methylpentyl-n-octyl ether. The compounds 1,3-di-(2-ethylhexyl)cyclohexane (Cetiol® S) and di-n-octyl ether (Cetiol® OE), available as commercial products, can be preferred.

Ester oils. "Ester oils" are to be understood as the esters of $C_6$ to $C_{30}$ fatty acids with $C_2$ to $C_{30}$ fatty alcohols. The monoesters of fatty acids with alcohols having 2 to 24 carbon atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid, as well as industrial mixtures thereof. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol, as well as industrial mixtures thereof. Particularly preferred according to the present invention are isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), Oleyl Oleate (Cetiol®), lauric acid hexyl ester (Cetiol® A), di-n-butyl adipate (Cetiol® B), myristyl myristate (Cetiol® MM), Cetearyl Isononanoate (Cetiol® SN), oleic acid decyl ester (Cetiol® V).

Dicarboxylic acid esters such as di-n-butyl adipate, di(2-ethylhexyl) adipate, di(2-ethylhexyl) succinate, and diisotridecyl acelaate, as well as diol esters such as ethylene glycol dioleate, ethylene glycol diisotridecanoate, propylene glycol di(2-ethyl hexanoate), propylene glycol diisostearate, propylene glycol dipelargonate, butanediol diisostearate, neopentyl glycol dicaprylate.

Symmetrical, asymmetrical, or cyclic esters of carbonic acid with fatty alcohols, for example glycerol carbonate or dicaprylyl carbonate (Cetiol® CC).

Mono-, di-, and trifatty acid esters of saturated and/or unsaturated linear and/or branched fatty acids with glycerol, for example Monomuls® 90-018, Monomuls® 90-L12, or Cutina® MD.

The quantity used is 0.1 to 50 wt. % based on the total agent, preferably 0.1 to 20 wt. %, and particularly preferably 0.1 to 15 wt. % based on the total agent.

The total quantity of oily and fatty components in the agents according to the present invention is usually 6 to 45 wt. %, based on the total agent. Quantities from 10 to 35 wt. % are preferred according to the present invention.

It has furthermore been shown that the effect of the active substance according to the present invention can be enhanced when it is combined with hydroxycarboxylic acid esters. Preferred hydroxycarboxylic acid esters are full esters of glycolic acid, lactic acid, malic acid, tartaric acid, or citric acid. Further hydroxycarboxylic acid esters that are suitable in principle are esters of β-hydroxypropionic acid, of tartronic acid, of D-gluconic acid, saccharic acid, mucic acid, or glucuronic acid. Primary linear or branched aliphatic alcohols having 8 to 22 carbon atoms, i.e., for example, fatty alcohols or synthetic fatty alcohols, are suitable as alcohol components of these esters. The esters of $C_{12}$ to $C_{15}$ fatty alcohols are particularly preferred. Esters of this type are available commercially, e.g. under the trademark Cosmacol® of EniChem, Augusta Industriale. The quantity of hydroxycarboxylic acid esters used is 0.1 to 15 wt. % based on the agent, preferably 0.1 to 10 wt. %, and very particularly preferably 0.1 to 5 wt. %.

As a further ingredient, the agents used according to the present invention can, with particular preference, include one or more amino acids. Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cys), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, in which context both the individual amino acids and mixtures can be used.

Preferred agents according to the present invention include one or more amino acids in narrower quantity ranges. Hair treatment agents preferred according to the present invention are characterized here in that they include as a care-providing substance, based on their weight, 0.01 to 5 wt. %, by preference 0.02 to 2.5 wt. %, particularly preferably 0.05 to 1.5 wt. %, more preferably 0.075 to 1 wt. %, and in particular 0.1 to 0.25 wt. % amino acid(s), by preference from the group of glycine and/or alanine and/or valine and/or lysine and/or leucine and/or threonine.

A further preferred group of ingredients of the agents according to the present invention are the vitamins, provitamins, or vitamin precursors. These are described below:

The group of substances referred to as "vitamin A" includes retinol (vitamin $A_1$) as well as 3,4-didehydroretinol (vitamin $A_2$). n-Carotene is the provitamin of retinol. Vitamin A components that are suitable according to the present invention are, for example, vitamin A acid and esters thereof, vitamin A aldehyde, and vitamin A alcohol, as well as esters thereof such as the palmitate and acetate. The agents used according to the present invention include the vitamin A component preferably in quantities from 0.05 to 1 wt. %, based on the total preparation.

Members of the vitamin B group or vitamin B complex are, among others:

Vitamin $B_1$ (thiamine)

Vitamin $B_2$ (riboflavin)

Vitamin $B_3$. The compounds nicotinic acid and nicotinic acid amide (niacinamide) are often listed under this designation. Nicotinic acid amide is preferred according to the present invention; it is included in the agents used according to the present invention preferably in quantities from 0.05 to 1 wt. % based on the total agent.

Vitamin $B_5$ (pantothenic acid, panthenol, and pantolactone). In the context of this group, panthenol and/or pantolactone are preferably used. Derivatives of panthenol that are usable according to the present invention are, in particular, the esters and ethers of panthenol as well as cationically derivatized panthenols. Individual representatives are, for example, panthenol triacetate, panthenol monoethyl ether and its monoacetate, and cationic panthenol derivatives. The aforesaid compounds of the vitamin $B_5$ type are included in the agents according to the present invention preferably in quantities from 0.05 to 10 wt. % based on the total agent. Quantities from 0.1 to 5 wt. % are particularly preferred.

Vitamin $B_6$ (pyridoxine as well as pyridoxamine and pyridoxal).

Vitamin C (ascorbic acid). Vitamin C is utilized in the agents according to the present invention preferably in quantities from 0.1 to 3 wt. % based on the total agent. Utilization in the form of the palmitic acid ester, the glucosides, or the phosphates can be preferred. Utilization in combination with tocopherols can likewise be preferred.

Vitamin E (tocopherols, in particular α-tocopherol). Tocopherol and its derivatives, which include in particular the esters such as the acetate, the nicotinate, the phosphate, and the succinate, are included in the agents according to the present invention preferably in quantities from 0.05 to 1 wt % based on the total agent.

Vitamin F. The term "vitamin F" is usually understood to mean essential fatty acids, in particular linoleic acid, linolenic acid, and arachidonic acid.

Vitamin H. "Vitamin H" refers to the compound (3aS,4S,6aR)-2-oxohexahydrothienol[3,4-d]-imidazole-4-valeric acid, for which the trivial name "biotin" has, however, now become established. Biotin is included in the agents according to the present invention preferably in quantities from 0.0001 to 1.0 wt. %, in particular in quantities from 0.001 to 0.01 wt. %.

In summary, preferred hair treatment agents according to the present invention are those that additionally include as a care-providing substance, based on their weight, 0.1 to 5 wt. %, by preference 0.2 to 4 wt. %, particularly preferably 0.25 to 3.5 wt. %, more preferably 0.5 to 3 wt. %, and in particular 0.5 to 2.5 wt. % vitamins and/or provitamins and/or vitamin precursors that are allocated by preference to the groups A, B, C, E, F, and H; preferred agents include panthenol ((±)-(2,4-dihydroxy-N-(3-hydroxypropyl)-3,3-dimethylbutyramide, provitamin $B_5$) and/or panthothenic acid (vitamin $B_3$, vitamin $B_5$) and/or niacin, niacinamide resp. nicotinamide (vitamin $B_3$) and/or L-ascorbic acid (vitamin C) and/or thiamine (vitamin $B_1$) and/or riboflavin (vitamin $B_2$, vitamin G) and/or biotin (vitamin $B_7$, vitamin H) and/or folic acid (vitamin $B_9$, vitamin $B_e$ or vitamin M) and/or vitamin $B_6$ and/or vitamin $B_{12}$.

It has been found that the use of certain quinones intensifies an effect counteracting dandruff and hair loss, and provides advantages with regard to combability and shine. The agents according to the present invention can therefore to be understood as a further constituent 0.0001 to 5 wt. % of at least one bioquinone and/or plastoquinone. The ubiquinones preferred according to the present invention have the following formula:

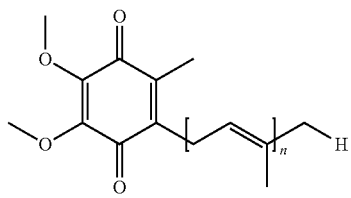

where n = 6, 7, 8, 9, or 10.

Coenzyme Q-10 is the most preferred in this context.

To improve the elasticity and strengthen the internal structure of the hair treated with the agents according to the present invention, the agents according to the present invention can include purine and/or purine derivatives. In particular, the result of combining purine and/or purine derivatives with ubiquinones and/or plastoquinones is that the hair treated with corresponding agents exhibits, inter alia, higher measured values in differential thermal analysis, and improved wet and dry combability values.

Preferred compositions according to the present invention include purine and/or purine derivatives in narrower quantity ranges. Cosmetic agents preferred according to the present invention are characterized here in that they include, based on their weight, 0.001 to 2.5 wt. %, by preference 0.0025 to 1 wt. %, particularly preferably 0.005 to 0.5 wt. %, and in particular 0.01 to 0.1 wt. % purine(s) and/or purine derivative(s). Cosmetic agents preferred according to the present invention are characterized in that they include purine, adenine, guanine, uric acid, hypoxanthine, 6-purinethiol, 6-thioguanine, xanthine, caffeine, theobromine, or theophylline. In hair-cosmetic preparations, caffeine is the most preferred.

It is further advantageous to use purine resp. purine derivatives and bioquinones at a specific ratio to one another. Preferred in this context are agents according to the present invention in which the weight ratio of ingredients a) and b) is equal to 10:1 to 1:100, by preference 5:1 to 1:50, particularly preferably 2:1 to 1:20, and in particular 1:1 to 1:10.

As already mentioned, caffeine is a particularly preferred purine derivative, and Coenzyme Q10 is a particularly preferred bioquinone. Particularly preferred agents according to the present invention are therefore characterized in that they include, based on their weight, 0.001 to 2.5 wt. %, by preference 0.0025 to 1 wt. %, particularly preferably 0.005 to 0.5 wt. %, and in particular 0.01 to 0.1 wt. % caffeine, and 0.0002 to 4 wt. %, by preference 0.0005 to 3 wt. %, particularly preferably 0.001 to 2 wt. %, more preferably 0.0015 to 1, and in particular 0.002 to 0.5 wt. % Coenzyme Q10.

As a further constituent, the agents according to the present invention can include at least one carbohydrate from the group of the monosaccharides, disaccharides, and/or oligosaccharides. Hair treatment agents preferred according to the present invention are characterized here in that they include as a care-providing substance, based on their weight, 0.01 to 5 wt. %, by preference 0.05 to 4.5 wt. %, particularly preferably 0.1 to 4 wt. %, more preferably 0.5 to 3.5 wt. %, and in particular 0.75 to 2.5 wt. % carbohydrate(s) selected from monosaccharides, disaccharides, and/or oligosaccharides, preferred carbohydrates being selected from monosaccharides, in particular D-ribose and/or D-xylose and/or -arabinose and/or D-glucose and/or D-mannose and/or D-galactose and/or D-fructose and/or sorbose and/or L-fucose and/or L-rhamnose, disaccharides, in particular sucrose and/or maltose and/or lactose and/or trehalose and/or cellobiose and/or gentobiose and/or isomaltose.

Particularly preferred agents according to the present invention include, based on their weight, 0.005 to 0.015 wt. % caffeine and 0.75 to 1.5 wt. % glucose monohydrate, 0.005 to 0.015 wt. % caffeine and 0.75 to 1.5 wt. % sucrose, 0.005 to 0.015 wt. % caffeine and 0.75 to 1.5 wt. % fructose.

As already mentioned, preferred agents according to the present invention include (an) amino acids(s).

Amino acids usable particularly preferably according to the present invention derive from the group of glycine, alanine, valine, leucine, isoleucine, phenylalanine, tyrosine, tryptophan, proline, aspartic acid, glutamic acid, asparagine, glutamine, serine, threonine, cysteine, methionine, lysine, arginine, histidine, β-alanine, 4-aminobutyric acid (GABA), betaine, L-cystine (L-cyss), L-carnitine, L-citrulline, L-theanine, 3',4'-dihydroxy-L-phenylalanine (L-DOPA), 5'-hydroxy-L-tryptophan, L-homocysteine, S-methyl-L-methionine, S-allyl-L-cysteine sulfoxide (L-alliin), L-trans-4-hydroxyproline, L-5-oxoproline (L-pyroglutamic acid), L-phosphoserine, creatine, 3-methyl-L-histidine, L-ornithine, in which context both the individual amino acids and mixtures can be used.

Preferred agents according to the present invention include one or more amino acids in narrower quantity ranges. Cosmetic agents preferred according to the present invention are characterized here in that they additionally include 0.05 to 5 wt. %, by preference 0.1 to 2.5 wt. %, particularly preferably 0.15 to 1 wt. %, and in particular 0.2 to 0.5 wt. % amino acid(s), by preference (an) amino acid(s) from the group of glycine and/or alanine and/or valine and/or lysine and/or leucine and/or threonine.

A further, preferably usable care-providing substance that possesses activating properties is taurine. Hair treatment agents preferred according to the present invention include as a care-providing substance, based on their weight, 0.01 to 15 wt. %, by preference 0.025 to 12.5 wt. %, particularly preferably 0.05 to 10 wt. %, more preferably 0.1 to 7.5 wt. %, and in particular 0.5 to 5 wt. % taurine (2-aminoethanesulfonic acid).

The additional use of bisabolol and/or bisabolol oxides in the agents according to the present invention is also preferred. Hair treatment agents according to the present invention that additionally include 0.001 to 5 wt. %, by preference 0.01 to 4 wt. %, particularly preferably 0.02 to 2.5 wt. %, and in particular 0.1 to 1.5 wt. % bisabolol and/or oxides of bisabolol, by preference (-)-alpha-bisabolol, are preferred here.

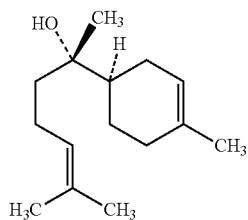 [SMILES: CC(C)=CCC[C@](C)(O)[C@H]1CC=C(C)CC1]

In a preferred embodiment of the invention, an agent according to the present invention can furthermore also include UV filters (I). The UV filters to be used according to the present invention are not subject to any general restrictions in terms of their structure and their physical properties. Instead, all UV filters usable in the cosmetics sector, whose absorption maximum lies in the UVA (315 to 400 nm) UVB (280 to 315 nm), or UVC (<280 nm) regions, are suitable. UV filters having an absorption maximum in the UVB region, in particular in the region from approximately 280 to approximately 300 nm, are particularly preferred.

The UV filters used according to the present invention can be selected, for example, from substituted benzophenones, p-aminobenzoic acid esters, diphenylacrylic acid esters, cinnamic acid esters, salicylic acid esters, benzimidazoles, and o-aminobenzoic acid esters.

Examples of UV filters usable according to the present invention are 4-aminobenzoic acid, N,N,N-trimethyl-4-(2-oxobom-3-ylidenemethyl)aniline methylsulfate, 3,3,5-trimethylcyclohexyl salicylate (Homosalate), 2-hydroxy-4-methoxybenzophenone (Benzophenone-3; Uvinul® M 40, Uvasorb® MET, Neo Heliopan® BB, Eusolex® 4360), 2-phenylbenzimidazole-5-sulfonic acid and potassium, sodium, and triethanolamine salts thereof (phenylbenzimidazolesulfonic acid; Parsol® HS; Neo Heliopan® Hydro), 3,3'-(1,4-phenylenedimethylene)-bis(7,7-dimethyl-2-oxo-bicyclo-[2.2.1]hept-1-yl-methanesulfonic acid) and salts thereof, 1-(4-tert-butylphenyl)-3-(4-methoxyphenyl)propane-1,3-dione (butylmethoxydibenzoylmethane; Parsol® 1789, Eusolex® 9020), α-(2-oxobom-3-ylidene)toluene-4-sulfonic acid and salts thereof, ethoxylated 4-aminobenzoic acid ethyl ester (PEG-25 PABA; Uvinul® P 25), 4-dimethylaminobenzoic acid 2-ethylhexyl ester (Octyl Dimethyl PABA; Uvasorb® DMO, Escalol® 507, Eusolex® 6007), salicylic acid 2-ethylhexyl ester (Octyl Salicylate; Escalol® 587, Neo Heliopan® OS, Uvinul® 018), 4-methoxycinnamic acid isopentyl ester (Isoamyl p-Methoxycinnamate; Neo Heliopan® E 1000), 4-methoxycinnamic acid 2-ethylhexyl ester (Octyl Methoxycinnamate; Parsol® MCX, Escalol® 557, Neo Heliopan® AV), 2-hydroxy-4-methoxybenzophenone-5-sulfonic acid and the sodium salt thereof (Benzophenone-4; Uvinul® MS 40; Uvasorb® S 5), 3-(4'-methylbenzylidene) D,L-camphor (4-Methylbenzylidene Camphor; Parsol® 5000, Eusolex® 6300), 3-benzylidene camphor (3-Benzylidene Camphor), 4-isopropylbenzyl salicylate, 2,4,6-trianilino-(p-carbo-2'-ethylhexyl-1'-oxi)-1,3,5-triazine, 3-imidazol-4-ylacrylic acid and ethyl esters thereof, polymers of N-{(2 and 4)-[2-oxoborn-3-ylidenemethyl]benzyl}acrylamide, 2,4-dihydroxybenzophenone (Benzophenone-1; Uvasorb® 20 H, Uvinul® 400), 1,1'-diphenylacrylonitrilic acid 2-ethylhexyl ester (Octocrylene; Eusolex® OCR, Neo Heliopan® Type 303, Uvinul® N 539 SG), o-aminobenzoic acid menthyl ester (Menthyl Anthranilate; Neo Heliopan® MA), 2,2',4,4'-tetrahydroxybenzophenone (Benzophenone-2; Uvinul® D-50), 2,2'-dihydroxy-4,4'-dimethoxybenzophenone (Benzophenone-6), 2,2'-dihydroxy-4,4'-dimethoxybenzophenone-5-sodiumsulfonate, and 2-cyano-3,3-diphenylacrylic acid 2'-ethylhexyl ester. 4-Aminobenzoic acid, N,N,N-trimethyl-4-(2-oxobom-3-ylidenemethyl)aniline methyl sulfate, 3,3,5-trimethylcyclohexyl salicylate, 2-hydroxy-4-methoxybenzophenone, 2-phenylbenzimidazole-5-sulfonic acid and potassium, sodium, and triethanolamine salts thereof, 3,3'-(1,4-phenylenedimethylene)-bis(7,7-dimethyl-2-oxo-bicyclo-[2.2.1] hept-1-ylmethanesulfonic acid) and salts thereof, 1-(4-tert-butylphenyl)-3-(4-methoxyphenyl)propane-1,3-dione, α-(2-oxoborn-3-ylidene)toluene-4-sulfonic acid and salts thereof, ethoxylated 4-aminobenzoic acid ethyl ester, 4-dimethylaminobenzoic acid 2-ethylhexyl ester, salicylic acid 2-ethylhexyl ester, 4-methoxycinnamic acid isopentyl ester, 4-methoxycinnamic acid 2-ethylhexyl ester, 2-hydroxy-4-methoxybenzophenone-5-sulfonic acid and the sodium salt thereof, 3-(4'-methylbenzylidene) D,L-camphor, 3-benzylidene camphor, 4-isopropylbenzyl salicylate, 2,4,6-trianilino-(p-carbo-2'-ethylhexyl-1'-oxi)-1,3,5-triazine, 3-imidazol-4-ylacrylic acid and ethyl esters thereof, and polymers of N-{(2 and 4)-[2-oxoborn-3-ylidenemethyl]benzyl}acrylamide are preferred. Very particularly preferred according to the present invention are 2-hydroxy-4-methoxybenzophenone, 2-phenylbenzimidazole-5-sulfonic acid and potassium, sodium, and triethanolamine salts thereof, 1-(4-tert-butylphenyl)-3-(4-methoxyphenyl)propane-1,3-dione, 4-methoxycinnamic acid 2-ethylhexyl ester, and 3-(4'-methylbenzylidene) D,L-camphor.

Those UV filters whose molar extinction coefficient at the absorption maximum is above 15,000, in particular above 20,000, are preferred.

It has furthermore been found that with structurally similar UV filters, in the context of the teaching of the present invention the water-insoluble compound in many cases exhibits the greater effectiveness as compared with those water-soluble compounds that differ from it by having one or more additionally ionic groups. In the context of the invention, those UV filters of which no more than 1 wt. %, in particular no more than 0.1 wt. %, dissolves in water at 20° C., are understood to be "water-insoluble." These compounds should furthermore be soluble at a proportion of at least 0.1, in particular at least 1 wt. %, in common cosmetic oil components at room temperature. The use of water-insoluble UV filters can therefore be preferred according to the present invention.

According to a further embodiment of the invention, those UV filters that comprise a cationic group, in particular a quaternary ammonium group, are preferred.

Two preferred UV filters having cationic groups are the compounds cinnamic acid amidopropyltrimethylammonium chloride (Incroquat® UV-283) and dodecyldimethylaminobenzamidopropyldimethylammonium tosylate (Escalol® HP 610), available as commercial products.

The teaching of the present invention of course also encompasses the use of a combination of several UV filters. In the context of this embodiment, the combination of at least one water-insoluble UV filter with at least one UV filter having a cationic group is preferred.

The UV filters (I) are included in the agents according to the present invention usually in quantities from 0.1 to 5 wt. % based on the total agent. Quantities from 0.4 to 2.5 wt. % are preferred.

The agents according to the present invention can furthermore include a 2-pyrrolidone-5-carboxylic acid and derivatives thereof (J). The sodium, potassium, calcium, magnesium, or ammonium salts, in which the ammonium ion carries one to three $C_1$ to $C_4$ alkyl groups in addition to hydrogen, are preferred. The sodium salt is very particularly preferred. The quantities used in the agents according to the present invention are by preference 0.05 to 10 wt. % based on the entire agent, particularly preferably 0.1 to 5, and in particular 0.1 to 3 wt. %.

Lastly, the agents used according to the present invention can also include plant extracts (L).

These extracts are usually produced by extraction of the entire plant. In individual cases, however, it may also be preferred to produce the extracts exclusively from blossoms and/or leaves of the plant.

With regard to the plant extracts usable according to the present invention, reference is made in particular to the extracts that are listed in the table beginning on page 44 of the 3rd edition of the Guideline for declaring the contents of cosmetic agents [Leitfaden zur Inhaltsstoffdeklaration kosmetischer Mittel] published by the Association of the personal hygiene and washing agents industry [Industrieverband Körperpflege- and Waschmittel e.V. (IKW)], Frankfurt.

According to the present invention the extracts from green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root are especially preferred.

Particularly preferred are the extracts from green tea, oak bark, nettle, hamamelis, hops, chamomile, burdock root, horsetail, linden blossoms, almond, aloe vera, coconut, mango, apricot, lemon, wheat, kiwi fruit, melon, orange, grapefruit, salvia, rosemary, birch, lady's-smock, wild thyme, yarrow, restharrow, meristem, ginseng, and ginger root.

The extracts from green tea, almond, aloe vera, coconut, mango, apricot, lemon, wheat, kiwi fruit, and melon are very particularly suitable for the use according to the present invention.

According to the present invention the plant extracts can be used in both pure and diluted form. If they are used in diluted form, they usually include approx. 2 to 80 wt. % active substance, and include as a solvent the extraction agent or extraction agent mixture used to obtain them.

It may furthermore be preferred to use mixtures of several, in particular two, different plant extracts in the agents according to the present invention.

In addition, it may prove advantageous if penetration adjuvants and/or swelling agents (M) are included in the agents used according to the present invention. To be included thereamong are, for example, urea and urea derivatives, guanidine and derivatives thereof, arginine and derivatives thereof, water glass, imidazole and derivatives thereof, histidine and derivatives thereof, benzyl alcohol, glycerol, glycol and glycol ethers, propylene glycol and propylene glycol ethers, for example propylene glycol monoethyl ether, carbonates, hydrogen carbonates, diols and triols, and in particular 1,2-diols and 1,3-diols such as, for example, 1,2-propanediol, 1,2-pentanediol, 1,2-hexanediol, 1,2-dodecanediol, 1,3-propanediol, 1,6-hexanediol, 1,5-pentanediol, 1,4-butanediol.

The agents according to the present invention have advantageous properties, and likewise impart advantageous properties to the hair treated therewith. Advantages are observed in particular in the context of hair conditioning. For example, hair treatment agents according to the present invention improve the softness and combability, in the dry and wet states, of the hair treated with them. Prevention of premature splitting of the treated hair is also evident, with no impairment of volume and fullness.

A further subject of the present invention is therefore a method for providing care to human hair, in which an agent according to the present invention is applied onto the hair, is left on the hair for a contact time from 10 to 600 seconds, preferably from 30 to 150 seconds, and the hair is then rinsed out.

Also a subject of the present invention is a method for providing care to human hair in which an agent according to the present invention is applied onto the hair and is left there until the next hair washing, i.e. is not rinsed out after a contact time of a few seconds.

This procedure according to the present invention is based on a product according to the present invention that is formulated as a so-called "rinse-off" product, i.e. the product remains in the hair for a period of time of less than a quarter of an hour, and is then rinsed out. Surprisingly, it is possible with the rinse-off products according to the present invention to achieve care-providing results that equal or in fact exceed those of conventional leave-in products.

The statements made with respect to the agents according to the present invention apply, mutatis mutandis, with regard to further preferred embodiments of the methods according to the present invention.

A further subject of the present invention is the use of agents according to the present invention for non-weighing hair care.

The statements made with respect to the agents according to the present invention apply, mutatis mutandis, with regard to further preferred embodiments of the use according to the present invention.

EXAMPLES

Care-providing agents of the following composition (indications in wt. % based on the total agent) were manufactured using methods known per se to the skilled artisan:

|  | A | B | C | D | E |
|---|---|---|---|---|---|
| Cetrimonium chloride | 0.2 | 0.5 | 0.2 | 0.5 | 0.5 |
| PEG-40 Dimethicone | 0.35 | — | 0.35 | — | — |
| Cyclomethicone | 3.0 | 10.0 | 3.0 | 10.0 | 10.0 |
| Dimethiconol | — | 4.5 | 4.5 | 4.5 | — |
| Polyquaternium-16 | — | 1.0 | — | 1.0 | 1.0 |
| Sodium benzoate | 0.1 | 0.1 | 0.1 | 0.1 | 0.1 |
| D-panthenol, 75% | 0.5 | 0.5 | 0.5 | 0.5 | 0.5 |
| Dow Corning ® 556 | 0.3 | 3.0 | 0.3 | 3.0 | 3.0 |
| Lactic acid, 80% | 0.75 | 0.75 | 0.75 | 0.75 | 0.75 |
| Cationic wheat hydrolysate | 1.0 | 1.0 | 1.0 | 1.0 | 1.0 |
| Cetyl PEG/PPG 10/1 Dimethicone | 0.1 | 1.5 | 0.1 | 1.5 | 1.2 |
| Lauryl PEG/PPG 18/18 Dimethicone | — | — | 0.3 | 1.2 | 0.3 |
| Water, deionized | to 100 | to 100 | to 100 | to 100 | to 100 |

The agents were applied onto untreated human hair, and rinsed out after 5 minutes with warm water. The untreated and treated hair was investigated using differential thermal analysis, in which the peak temperature indicates the extent to which the matrix and the alpha helix are stable. The higher the peak temperature, the more stable the hair structure.

The hair treated with agents according to the present invention exhibited after treatment, on average, a peak temperature elevated by 3° C. (153° C. rather than 150° C.). For comparison, hair was treated with a commercially usual leave-in treatment. This comparison sample yielded only a 1° C. increase in peak temperatures.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A hair treatment agent comprising, based on its weight,
   a) at least 70 wt. % water,
   b) 0.1 to 1.5 wt. % of at least one silicone-based water-in-oil emulsifier from the group of C8 to C30 alkyl PEG/PPG dimethicone,
   c) 1 to 10 wt. % cyclic siloxane,
   d) at least 0.1 to 5 wt. % of a cationic protein hydrolysate, and
   e) one or more cationic surfactants as emulsifiers, wherein all of the cationic surfactants included in the agent are silicone free,
   wherein the hair treatment agent is characterized to form, within 10 minutes of mixing, a two-phase composition that has a lower aqueous phase and an upper oil phase.

2. The agent according to claim 1, wherein the at least one silicone-based water-in-oil emulsifier from the group of C8 to C30 alkyl PEG/PPG dimethicones is included at a concentration ranging between 0.15 and 1.25 wt. %.

3. The agent according to claim 1, wherein the cyclic siloxane is included at a concentration ranging between 1.5 and 9.5 wt. %.

4. The agent according to claim 1, wherein the silicone-based water-in-oil emulsifier from the group of C8 to C30 alkyl PEG/PPG dimethicones is selected from lauryl, myristyl, cetyl, and/or stearyl PEG/PPG dimethicones.

5. The agent according to claim 1, wherein the cationic protein hydrolysate is a plant-based cationic protein hydrolysate.

6. The agent according to claim 5, wherein the cationic protein hydrolysate is a cationic wheat protein hydrolysate.

7. The agent according to claim 1, wherein the agent further comprises, based on its weight, 0.05 to 7.5 wt. % of one or more cationic polymers selected from the group consisting of:
   poly(methacryloyloxyethyltrimethylammonium chloride) (INCI: Polyquaternium-37),
   quaternized cellulose derivatives (INCI: Polyquaternium-10),
   cationic alkylpolyglycosides,
   cationized honey,
   cationic guar derivatives,
   polymeric dimethyldiallylammonium salts and copolymers thereof with esters and amides of acrylic acid and methacrylic acid,
   copolymers of vinylpyrrolidone with quaternized derivatives of dialkylaminoalkyl acrylate and methacrylate,
   vinylpyrrolidone-vinylimidazolium methochloride copolymers, quaternized polyvinyl alcohol,
Polyquaternium-2,
Polyquaternium-7,
Polyquaternium-16,
Polyquaternium-17,
Polyquaternium-18,
Polyquaternium-24, and
Polyquaternium-27.

8. A method for providing care to human hair, comprising:
applying an agent according to claim 1 onto the hair;
leaving the agent on the hair for a contact time from 10 to 600 seconds; and
rinsing the hair out.

* * * * *